(12) United States Patent
Hamm et al.

(10) Patent No.: US 8,175,682 B2
(45) Date of Patent: May 8, 2012

(54) TRANSDUCER/SENSOR ASSEMBLY

(75) Inventors: Mark Hamm, Lynnfield, MA (US); Louis J. Barbato, Franklin, MA (US); Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/240,823

(22) Filed: Sep. 22, 2011

(65) Prior Publication Data
US 2012/0010466 A1 Jan. 12, 2012

Related U.S. Application Data

(63) Continuation of application No. 13/098,239, filed on Apr. 29, 2011, now Pat. No. 8,052,603, which is a continuation of application No. 10/689,767, filed on Oct. 20, 2003, now Pat. No. 7,951,081.

(51) Int. Cl.
*A61B 5/05* (2006.01)

(52) U.S. Cl. ........ 600/424; 600/160; 600/437; 600/463; 600/427; 600/407

(58) Field of Classification Search .................. 600/407, 600/424, 427, 463, 437, 160
See application file for complete search history.

(56) References Cited

U.S. PATENT DOCUMENTS

| | | |
|---|---|---|
| 4,571,520 A | 2/1986 | Saito et al. |
| 4,802,487 A | 2/1989 | Martin et al. |
| 4,841,977 A | 6/1989 | Griffith et al. |
| 4,911,170 A | 3/1990 | Thomas, III et al. |
| 4,917,097 A | 4/1990 | Proudian et al. |
| 5,002,058 A | 3/1991 | Martinelli |
| 5,109,861 A | 5/1992 | Walinsky et al. |
| 5,115,810 A | 5/1992 | Watanabe et al. |
| 5,240,004 A | 8/1993 | Walinsky et al. |
| 5,243,988 A | 9/1993 | Whalen |
| 5,353,798 A | 10/1994 | Sieben |
| 5,368,035 A | 11/1994 | Hamm et al. |
| 5,503,154 A | 4/1996 | Belef |
| 5,577,506 A | 11/1996 | Dias |
| 5,738,100 A | 4/1998 | Yagami et al. |
| 5,902,245 A | 5/1999 | Yock |
| 5,947,905 A | 9/1999 | Hadjicostis et al. |
| 6,019,726 A | 2/2000 | Webb |

(Continued)

FOREIGN PATENT DOCUMENTS
EP 0894473 2/1999

OTHER PUBLICATIONS

Office Communication for U.S. Appl. No. 10/689,767 mailed Sep. 8, 2008.
Office Communication for U.S. Appl. No. 10/689,767 mailed Feb. 4, 2009.

(Continued)

*Primary Examiner* — Brian Casler
*Assistant Examiner* — Joel Lamprecht
(74) *Attorney, Agent, or Firm* — Frommer Lawrence & Haug LLP; Bruce E. Black

(57) ABSTRACT

An imaging transducer assembly is combined with a sensor of a medical positioning system, forming a transducer/sensor assembly. In one embodiment, the sensor includes a coil proximally coupled with the imaging transducer. A cable having first and second wires are proximally coupled to the coil. A non-conductive potting layer is wrapped around the coil. Traces are formed in the non-conductive potting layer that are used to electrically couple the imaging transducer with the first and second wires of the cable.

20 Claims, 4 Drawing Sheets

U.S. PATENT DOCUMENTS

| | | | |
|---|---|---|---|
| 6,024,739 | A | 2/2000 | Ponzi |
| 6,078,831 | A | 6/2000 | Belef et al. |
| 6,200,269 | B1 | 3/2001 | Lin et al. |
| 6,210,356 | B1 | 4/2001 | Anderson et al. |
| 6,248,074 | B1 | 6/2001 | Ohno et al. |
| 6,261,246 | B1 | 7/2001 | Pantages et al. |
| 6,283,920 | B1 | 9/2001 | Eberle et al. |
| 6,309,370 | B1 | 10/2001 | Haim et al. |
| 6,457,365 | B1 | 10/2002 | Stephens et al. |
| 6,529,760 | B2 | 3/2003 | Pantages et al. |
| 7,951,081 | B2 | 5/2011 | Hamm et al. |
| 8,052,603 | B2 | 11/2011 | Hamm et al. |
| 2003/0028096 | A1 | 2/2003 | Niwa et al. |
| 2004/0193041 | A1 | 9/2004 | Ostrovsky |
| 2005/0042424 | A1 | 2/2005 | Frey et al. |

OTHER PUBLICATIONS

Office Communication for U.S. Appl. No. 10/689,767 mailed May 22, 2009.

Office Communication for U.S. Appl. No. 10/689,767 mailed Dec. 8, 2009.

Office Communication for U.S. Appl. No. 10/689,767 mailed Mar. 17, 2010.

Office Communication for U.S. Appl. No. 10/689,767 mailed Feb. 2, 2011.

Office Communication for U.S. Appl. No. 13/098,239 mailed Sep. 8, 2011.

International Search Report and Written Opinion for International Patent Application No. PCT/US2004/033987 received Feb. 2, 2005.

International Preliminary Report on Patentability for International Patent Application No. PCT/US2004/033987 dated Apr. 24, 2006.

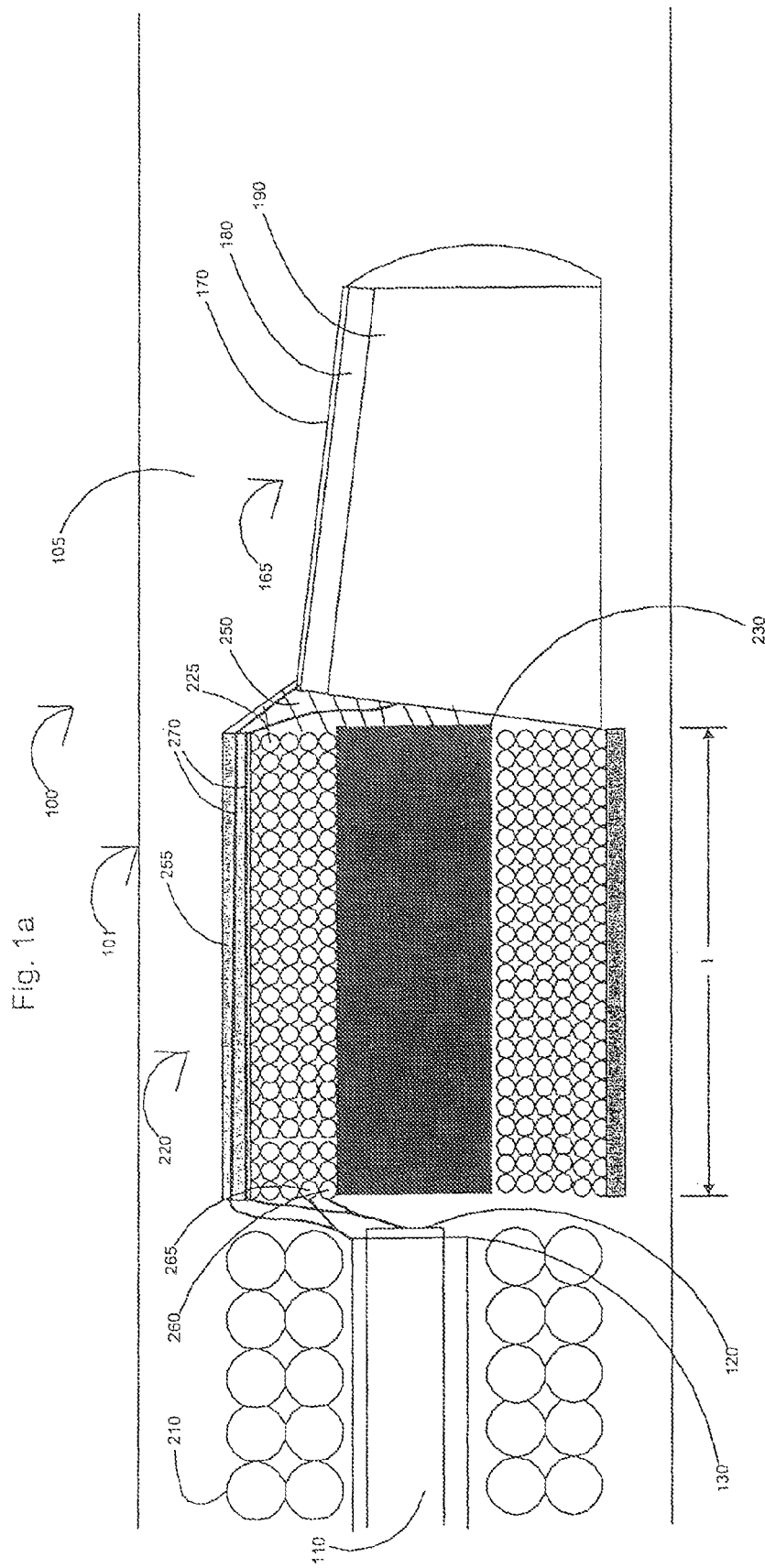

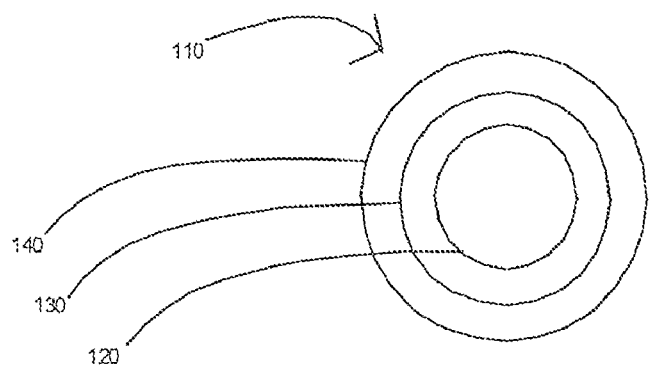
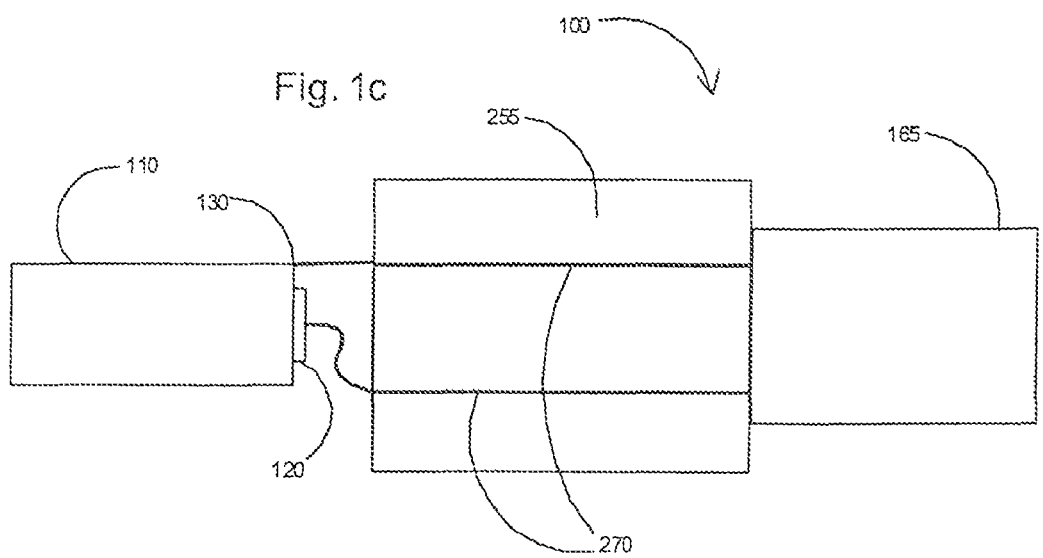

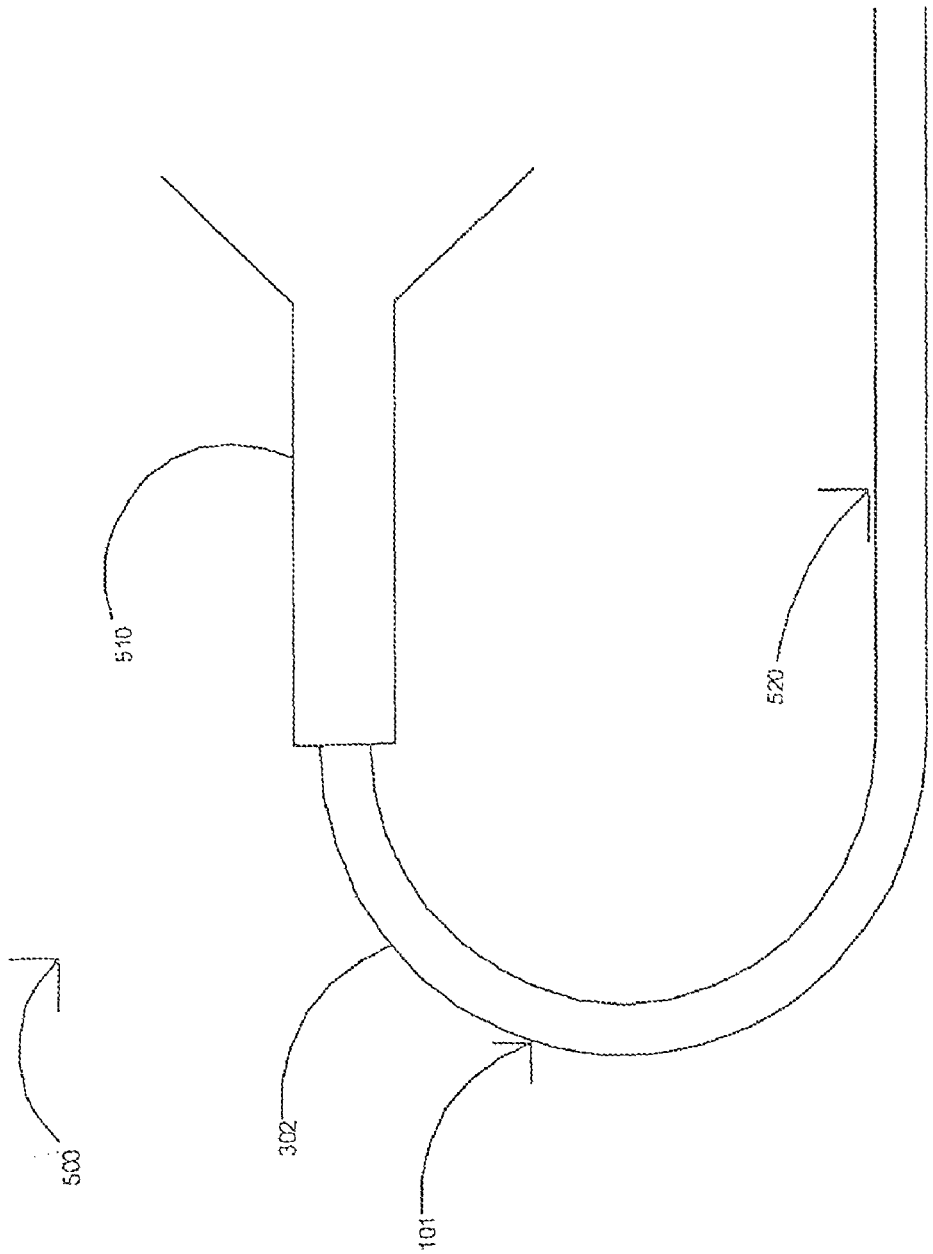

TRANSDUCER/SENSOR ASSEMBLY

CROSS-REFERENCE TO RELATED APPLICATIONS

This patent application is a continuation of U.S. patent application Ser. No. 13/098,239 filed Apr. 29, 2011 which is a continuation of U.S. patent application Ser. No. 10/689,767, now U.S. Pat. No. 7,951,081, filed on Oct. 20, 2003, both of which are incorporated herein by reference.

FIELD OF THE INVENTION

The field of the invention relates to medical imaging systems, and more particularly to an improved transducer/sensor assembly.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer.

Further, the catheter may also be equipped with a sensor adapted to communicate with a medical positioning system. For example, U.S. patent application Ser. No. 10/401,901, entitled "An Improved Imaging Transducer Assembly," filed on Mar. 28, 2003, which is hereby incorporated by reference in its entirety, describes a catheter having a sensor adapted to communicated with a medical positioning system coupled with an imaging transducer, forming a transducer/sensor assembly.

The transducer/sensor assembly is generally a rigid structure; however, the vessels through which the assembly is typically advanced are often tortuous, which create tight radii within the catheter. Thus, it is desirable to have the rigid portions, such as the transducer/sensor assembly, of the catheter be relatively small in length.

Accordingly, an alternative transducer/sensor assembly may be desirable.

SUMMARY OF THE INVENTION

The improved imaging device may be used within a lumen of the human body, e.g., inside a blood vessel. Generally, the imaging transducer assembly is combined with a sensor of a medical positioning system, forming a transducer/sensor assembly. One example embodiment is described here. In this embodiment, the sensor includes a coil proximally coupled with the imaging transducer. A cable having first and second wires are proximally coupled to the coil. A non-conductive potting layer is wrapped around the coil. Traces are formed in the non-conductive potting layer that are used to electrically couple the imaging transducer with the first and second wires of the cable.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 1a is a cross-sectional side view of a transducer/sensor assembly in accordance with an example embodiment of the invention;

FIG. 1b is a cross-sectional view of a coaxial cable within the transducer/sensor assembly of FIG. 1a;

FIG. 1c is a top view of the transducer/sensor assembly of FIG. 1a;

FIG. 1d is a simplified diagram of an electrical circuit formed by the transducer/sensor assembly of FIG. 1a; and FIG. 2 is a partial cross-sectional side view of a catheter in accordance with an example embodiment of the invention.

DETAILED DESCRIPTION OF THE PREFERRED EMBODIMENTS

Figure 1D:
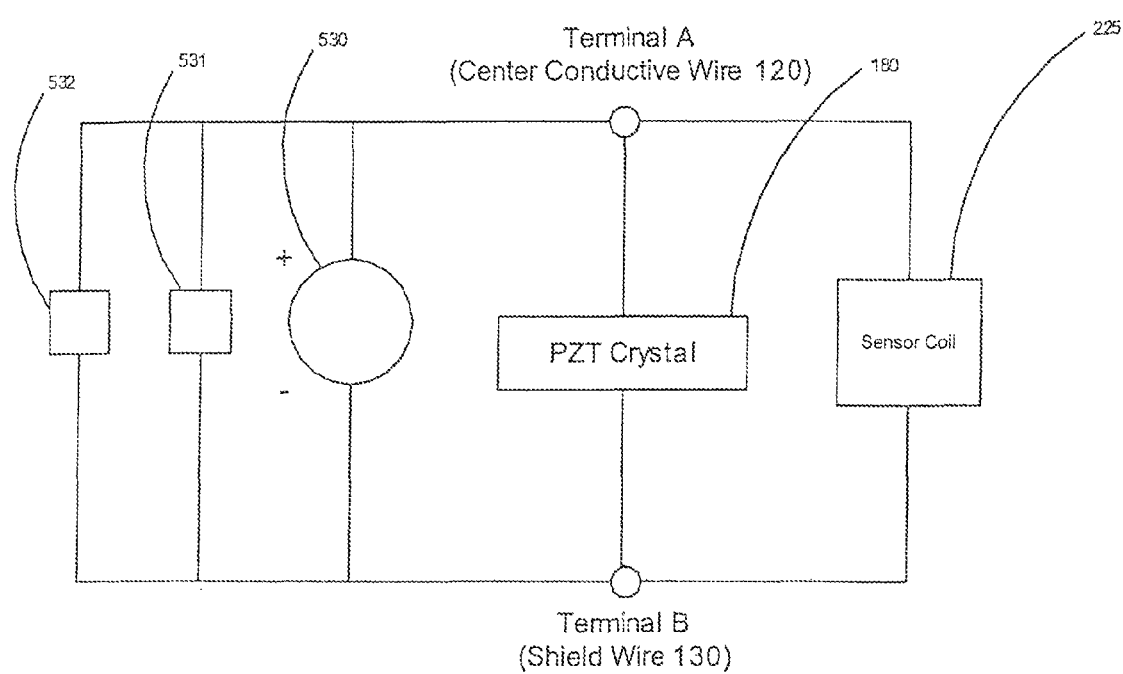

Described below is a catheter having an imaging transducer coupled with a sensor adapted to communicate with a medical positioning system, forming a transducer/sensor assembly.

Turning to FIG. 1a, a cross-sectional side view of a transducer/sensor assembly 100 is shown in a lumen 105 of the distal portion of a guidewire or catheter assembly (partially shown) having an outer tubular wall or sheath 101. The distal end of the transducer/sensor assembly 100 includes an imaging transducer 165. The imaging transducer 165 includes an electrically conductive backing material 190, having a top, bottom and center, which may be formed from an acoustically absorbent material (for example, an epoxy substrate having tungsten particles or silver particles). The top of the backing material 190 is coupled to the bottom of a layer of piezoelectric crystal (PZT) 180. The top of the PZT layer 180 is coupled to a conductive acoustic lens 170, which may include silver epoxy.

The transducer/sensor assembly 100 further includes a sensor 220 adapted to communicate with a medical positioning system. The sensor 220 includes an antenna portion, where the antenna transmits electro-magnetic signals to be received by an external receiver, (e.g., active transmission) or the antenna is otherwise detectable (e.g., passive) by an external receiver. The antenna portion includes a conductive wire wound into a first coil shape 225. The coil 225 may also have magnetic qualities. The sensor coil 225 is proximally coupled to the imaging transducer 165 via a non-conductive potting material 250. The potting material 250 may include parylene epoxy, or shrink tube. The sensor coil 225 is configured to send and/or receive electro-magnetic signals to and/or from transmitter/receiver nodes (not shown) surrounding a patient's body (not shown). Thus, as can be appreciated by one of ordinary skill in the art, it is preferable that the sensor coil 225 be configured to generate a sufficient magnetic flux density such that an effective sensor area is maintained to facilitate the sending and/or receiving of electro-magnetic signals.

The transducer/sensor assembly 100 is a rigid structure. As mentioned above, because the assembly 100 may travel through tortuous vessels, it may be preferable for the transducer/sensor assembly 100 to have a short length. One approach to reduce the length of the transducer/sensor assembly 100 is to reduce the length, l, of the sensor coil 225. However, if the sensor coil 225 length is reduced, the magnetic flux density may also be reduced. To compensate for this effect, the wire of the sensor coil 225 may be tightly wrapped around a solid magnetic core 230 of high magnetic permeability. The core 230 may alternatively be a non-magnetic core, such as "hi-mu 80" or a ferrite core. This configuration of the sensor coil 225 will increase the magnetic flux density of the sensor coil 225. Thus, the effective sensor area of the coil 225 may be maintained without having to increase the length, l, of the coil 225. With this configuration, the length of the transducer/sensor assembly 100 may be limited to preferably around 3 millimeters.

This configuration of the sensor coil 225 may also serve as a housing to reinforce the transducer/sensor assembly 100. The wire of the coil 225 is preferably copper and approximately 10 microns in diameter. The small diameter of the wire allows the sensor coil 225 to have a small impact on the dimensions of the transducer/sensor assembly 100, thus allowing the transducer/sensor assembly 100 to still work within the lumen 105 of the guidewire or catheter assembly. Because the lumen 105 is typically filled with a sonolucent liquid, such as saline, it is preferable to electrically isolate the sensor coil 225 from the lumen 105, thus substantially preventing potential signal noise. To achieve this electrical isolation, a thin layer of non-conductive potting material 255, such as non-conductive epoxy, or conformal coating such as parylene is applied over the sensor coil 225.

The transducer/sensor assembly 100 further includes a coaxial cable 110, having a center conductor wire 120, and an outer shield wire 130, as shown in FIG. 1b. The center conductor wire 120 is insulated from the outer shield wire 130. In addition, the shield wire 130 is surrounded by an insulating jacket 140. It should be noted that numerous alternative cable configurations may be used; for example, a cable having "shielded twisted pair" or "triaxial" wires may be used instead of a coaxial cable 110.

Turning back to FIG. 1a, surrounding the coaxial cable 110 is a drive shaft 210, which is a conductive wire wound around the coaxial cable 110 to form a second coil shape. Preferably, the conductive wire is stainless and has a diameter of approximately 500 microns. Because of the insulating jacket 140, the coaxial cable 110 is conductively insulated from the drive shaft 210. The drive shaft 210 and coaxial cable 110 are proximately coupled to the sensor coil 225.

Both the sensor coil 225 and the imaging transducer 165 transmit/receive power from the coaxial cable 110. The sensor coil 225 has a first terminal 265 and a second terminal 260. One of the center conductor wire 120 and the outer shield wire 130 of the coaxial cable 110 is coupled with one of the first 265 and second 260 terminals of the sensor coil 225 via electrically conductive epoxy, such as silver-filled epoxy. Further, the other of the center conductor wire 120 and the outer shield wire 130 of the coaxial cable 110 is coupled with the other of the first 265 and second 260 terminals of the sensor coil 225 also via electrically conductive epoxy, such as silver-filled epoxy.

Because the sensor coil 225 is wrapped tightly around a solid core 230, the coaxial cable 110 cannot be directly coupled with the imaging transducer 165. To electrically couple the coaxial cable 110 with the imaging transducer 165, shallow, wide trace conductors 270 may be formed in the non-conductive potting material 255 surrounding the sensor coil 225, as shown in FIG. 1c, which shows a top view of the transducer/sensor assembly 100. As can be appreciated by one of ordinary skill in the art, these trace conductors 270 may be formed in the potting material 255 using similar methods to forming traces on flexible circuit boards. For example, the trace conductors 270 may be painted in the potting material 255 using a conductive pen. Accordingly, one of the center conductor wire 120 and the outer shield wire 130 of the coaxial cable 110 is coupled with one of the trace conductors 270 via electrically conductive epoxy, such as silver-filled epoxy. Likewise, the other of the center conductor wire 120 and the outer shield wire 130 of the coaxial cable 110 is coupled with the other of trace conductors 270 via electrically conductive epoxy. It may be preferable to electrically isolate the trace conductors 270 from the lumen 105, thus, a non-conductive epoxy seal (not shown) or conformal coating, such as parylene may be applied over the trace conductors 270.

Alternatively, an additional insulated ultra-fine magnet wire (not shown), such as 58 g, may be used to create the electrical path across the sensor coil 225. The wire could be passed over or under the sensor coil 225 since its diameter is around 0.0005"(12.50 microns). This configuration may reduce the need for an additional insulating layer because the wire has its own insulating layer.

To electrically couple the imaging transducer 165 to the coaxial cable 110, one of the trace conductors 270 is coupled to one of the conductive acoustic lens 170 and the conductive backing material 190 via conductive epoxy formed within the potting material 250 between the sensor coil 225 and the imaging transducer 165. Further, the other trace conductor 270 is coupled to the other of the conductive acoustic lens 170 and the conductive backing material 190 via conductive epoxy formed within the potting material 250.

During the operation of the transducer/sensor assembly 100, the PZT crystal 180 is electrically excited by both the backing material 190 and the acoustic lens 170 both charged via the coaxial cable 110 and trace conductors 270. In addition, the sensor coil 225 may also be charged via the coaxial cable 110. If the sensor 220 is configured to send electromagnetic signals to nodes of a medical positioning system (not shown), then the charge may facilitate a broadcast. However, if the sensor 220 is configured to receive electromagnetic signals from one or more nodes of a medical positioning system (not shown), then separate circuitry including a signal processor, or proper timing to coincide with the "listen time'" of the transducer 165, may be used to filter and extract the desired electromagnetic signals. Thus, turning to FIG. 1d, the assembly 100 is depicted as a simplified electric circuit having a voltage source 530, the load of the PZT layer 180, the load of the sensor coil 225, which is in parallel with the load of the PZT layer 180, sensor circuitry 531, which may include a signal processor (not shown) to receive and process electromagnetic signals, i.e., navigational signals, from the sensor 220, as would be known to a person of skill in the art, transducer circuitry 532, which may also include a signal processor (not shown) to process imaging signals from the imaging transducer, and terminals A and B. Terminals A and B represent the center conductor wire 120 and the shield wire 130 of the coaxial cable 110, respectively. Other features and circuits may also be added as desired.

Turning to FIG. 2, the transducer/sensor assembly 100 may be placed in a distal portion 520 of a guidewire 500. The guidewire 500 may comprise a guidewire body 302 in the form of a flexible, elongate tubular member, having an outer wall 101. The guidewire body 302 may be formed of any material known in the art including nitinol hypotube, metal alloys, composite materials, plastics, braided polyimide, polyethylene, peek braids, stainless steel, or other superelastic materials.

The length of the guidewire 500 may vary depending on the application. In a preferred embodiment, the length of the guidewire 500 is between 30 cm and 300 cm. A catheter (not shown) may be configured to use several different diameters of guidewires 500. For example, the guidewire 500 may have a diameter of 0.010, 0.014, 0.018, or 0.035 inches. Typically, the diameter of the guidewire 500 is uniform.

A proximal portion 510 of the guidewire 500 may be adapted to connect to circuitry (not shown) that processes imaging signals from the imaging transducer and/or, circuitry (not shown) that processes navigational signals from the sensor 320, such circuits being well known.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. For example, this invention is particularly suited for applications involving medical imaging devices, but can be used on any design involving imaging devices in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed and desired to be protected by Letters Patent of the United States is:

1. An imaging catheter, comprising:
a sheath defining a lumen; and
an imaging assemble disposable within the lumen of the sheath and comprising
an imaging device,
an antenna coil positioned proximal to the imaging device,
a solid, non-conductive material disposed over at least a portion of the antenna coil and coupling the antenna coil to the imaging transducer, and
one or more traces formed over the antenna coil and disposed in the solid, non-conductive material, wherein the one or more traces are configured to electrically couple the imaging device to an energy source.

2. The imaging catheter of claim 1, further comprising a solid magnetic core around which the antenna coil is wrapped.

3. The imaging catheter of claim 1, further comprising a first wire and a second wire that are electrically coupled to the antenna coil, wherein the one or more traces are also electrically coupled with the first wire and the second wire.

4. The imaging catheter of claim 3, wherein the first and second wires are configured as a coaxial cable having an inner cable and an outer cable.

5. The imaging catheter of claim 3, wherein the first and second wires are configured as a shielded, twisted pair.

6. The imaging catheter of claim 1, further comprising a driveshaft disposed in the lumen of the sheath, wherein the imaging assembly is coupled to the driveshaft.

7. The imaging catheter of claim 1, wherein the imaging device comprises an imaging transducer.

8. The imaging catheter of claim 7, wherein the imaging transducer comprises a piezoelectric crystal, an acoustic lens coupled to the piezoelectric crystal, and a backing material coupled to the piezoelectric crystal.

9. The imaging catheter of claim 1, wherein the imaging transducer operates electrically in parallel with the antenna coil.

10. The imaging catheter of claim 1, further comprising a non-conductive seal disposed over the one or more traces.

11. A medical imaging system comprising:
a medical positioning system; and
the imaging catheter of claim 1.

12. A method of imaging within a body of a patient, the method comprising:
inserting the imaging catheter of claim 1 into the body of the patient;
operating the imaging device of the imaging catheter to obtain an image of a portion of the body of the patient; and
communicating between the antenna coil of the imaging catheter and an external medical positioning system to determine a position of the imaging assembly within the body of the patient.

13. The method of claim 12, wherein inserting the imaging catheter comprises inserting the imaging catheter into a blood vessel of the patient.

14. The method of claim 12, wherein communicating between the antenna coil of the imaging catheter and the external medical positioning system comprises sending an electromagnetic signal from the antenna coil to at least one node of the medical positioning system.

15. The method of claim 12, wherein communicating between the antenna coil of the imaging catheter and the external medical positioning system comprises receiving an electromagnetic signal from the medical positioning system at the antenna coil.

16. A method of making an imaging assembly, the method comprising:
coupling a sensor to an imaging transducer;
disposing a solid, non-conductive material over the sensor;
forming at least one trace conductor in the solid, non-conductive material; and
electrically coupling the at least one trace conductor to the imaging transducer.

17. The method of claim 16, wherein forming at least one trace conductor comprises painting the at least one trace conductor onto the solid, non-conductive material using a conductive pen.

18. The method of claim 16, further comprising coupling the at least one trace conductor to a coaxial cable.

19. The method of claim 16, further comprising disposing a non-conductive coating over the at least one trace conductor.

20. The method of claim 16, further comprising wrapping the antenna coil around a solid magnetic core.

\* \* \* \* \*